United States Patent
Banks et al.

(10) Patent No.: US 6,812,241 B2
(45) Date of Patent: Nov. 2, 2004

(54) NITROGEN-CONTAINING HETEROCYCLES HAVING PARASITICIDAL PROPERTIES

(75) Inventors: Bernard Joseph Banks, Sandwich (GB); Nathan Anthony Logan Chubb, Sandwich (GB)

(73) Assignee: Pfizer Inc., Kalamazoo, MI (US)

( * ) Notice: Subject to any disclaimer, the term of this patent is extended or adjusted under 35 U.S.C. 154(b) by 0 days.

(21) Appl. No.: 10/327,319

(22) Filed: Dec. 20, 2002

(65) Prior Publication Data

US 2003/0130307 A1 Jul. 10, 2003

Related U.S. Application Data

(62) Division of application No. 09/767,043, filed on Jan. 22, 2001, now Pat. No. 6,525,079, which is a division of application No. 09/567,330, filed on May 9, 2000, now abandoned, which is a continuation of application No. 09/452,423, filed on Dec. 1, 1999, now Pat. No. 6,110,958, which is a continuation of application No. 09/310,815, filed on May 12, 1999, now Pat. No. 6,083,965.

(30) Foreign Application Priority Data

May 14, 1998 (GB) ............................................ 9810354

(51) Int. Cl.[7] .................. A61K 31/4196; C07D 249/08
(52) U.S. Cl. ..................................... 514/383; 548/269.4
(58) Field of Search ....................... 548/269.4; 514/383

(56) References Cited

U.S. PATENT DOCUMENTS 5,223,525 A   6/1993  Wu et al. .................... 514/398
6,083,965 A   7/2000  Banks et al. ................. 514/359

FOREIGN PATENT DOCUMENTS

| EP | 285893 A2 | * 10/1988 | |
|---|---|---|---|
| EP | 0372982 | 6/1990 | ......... C07D/207/34 |
| EP | 0400842 | 12/1990 | ......... C07D/249/06 |
| EP | 0460940 | 12/1991 | ......... C07D/207/36 |
| EP | 0846686 | 6/1998 | ......... C07D/231/38 |
| JP | 6-92935 | 4/1994 | ......... C07D/209/30 |
| WO | WO9707102 | 2/1997 | ......... C07D/231/38 |
| WO | WO9804530 | 2/1998 | ......... C07D/231/38 |

* cited by examiner

*Primary Examiner*—Laura L. Stockton
(74) *Attorney, Agent, or Firm*—Martha G. Munchhof

(57) ABSTRACT

Compounds of formula (I)

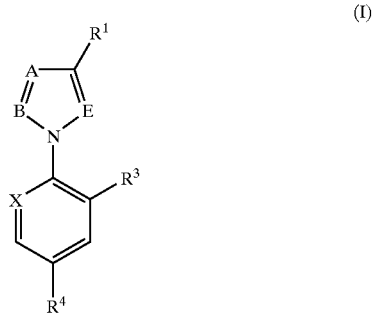

wherein the substituents are as defined herein, are antiparasitic agents.

11 Claims, No Drawings

NITROGEN-CONTAINING HETEROCYCLES HAVING PARASITICIDAL PROPERTIES

This application is a divisional application of U.S. patent application Ser. No. 09/767,043, filed Jan. 22, 2001, now U.S. Pat. No. 6,525,079, which is a divisional of U.S. patent application Ser. No. 09/567,330, filed May 9, 2000, now abandoned, which is a continuation of U.S. patent application Ser. No. 09/452,423, filed Dec. 1, 1999, now U.S. Pat. No. 6,110,958, which is a continuation of U.S. patent application Ser. No. 09/310,815, filed May 12, 1999, now U.S. Pat. No. 6,083,965, all of which are incorporated herein by reference.

This invention relates to nitrogen-containing heterocyclic substances having parasiticidal properties, in particular to N-aryl/heteroaryl-substituted heterocycles.

International Patent Application publication number WO98/24767 and European Patent Application publication number EP 0 846 686 A1 disclose certain 1-N-arylpyrazole substances with a 4-cyclopropyl moiety and a 4-heterocyclyl moiety respectively, as having antiparasitic properties.

According to the present invention, there is provided a compound of formula (I),

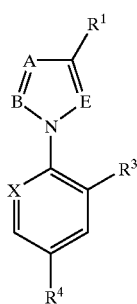

(I)

wherein A is N or $CR^5$,
B is N or $CR^6$,
wherein $R^5$ and $R^6$ are each independently selected from H, $C_{1-4}$ alkyl optionally substituted by one or more halo, CN and halo,
or when A and B are $CR^5$ and $CR^6$, respectively, they can be taken together to form a fused benzo- or pyridino-ring,
which fused ring is optionally substituted by one or two halo substituents and, when the pyridino-fused ring is present, optionally bears an oxide substituent on the nitrogen of said pyridino-ring,
$R^1$ is a 5-membered heteroaryl group selected from furan-2-yl, furan-3-yl, thien-2-yl, thien-3-yl and isoxazol-5-yl, each of which is optionally substituted by one or two substituents independently selected from halo, $C_{1-4}$ alkyl optionally substituted by one or more halo, and $(C_{1-4}$ alkyl optionally substituted by one or more halo)$S(O)_n$,
or $R^1$ is a group of formula (II)

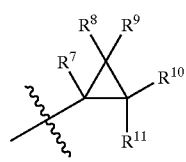

(II)

wherein $R^7$ is H, $C_{1-4}$ alkyl optionally substituted by one or more halo, or $C_{1-4}$ alkoxy optionally substituted by one or more halo, $R^8$ and $R^9$ are either each independently selected from H, chloro, fluoro, bromo and
$C_{1-4}$ alkyl optionally substituted by one or more halo, or, when taken together with the carbon atom to which they are attached, form a $C_{3-6}$ cycloalkyl group,
$R^{10}$ and $R^{11}$ are either each independently selected from H, chloro, fluoro, bromo and $C_{1-4}$ alkyl optionally substituted by one or more halo, or, when $R^8$ and $R^9$ taken together do not form part of a cycloalkyl group, $R^{10}$ and $R^{11}$ together with the carbon atom to which they are attached, form a $C_{5-7}$ cycloalkyl group,
E is N or $CR^2$, wherein
$R^2$ is H, $NH_2$, halo, $NHCH_2$(phenyl optionally substituted by $C_{1-4}$ alkoxy), $CO_2(C_{1-4}$ alkyl optionally substituted by one or more halo) or $S(O)_n(C_{1-4}$ alkyl optionally substituted by one or more halo),
X is N or $CR^{12}$, wherein
$R^{12}$ is halo,
$R^3$ is halo,
$R^4$ is $C_{1-4}$ alkyl optionally substituted by one or more halo, $C_{1-4}$ alkoxy optionally substituted by one or more halo, $S(O)_n(C_{1-4}$ alkyl optionally substituted by one or more halo), halo or $SF_5$, and
n is 0, 1 or 2,
with the provisos that (i) when B is N, then A and/or E is also N, and (ii) when E is N then A and/or B is also N,
or a pharmaceutically-, agriculturally- or veterinarily-acceptable salt thereof, or solvate of any such compound or salt (hereinafter referred to as "the substances of the invention").

Alkyl groups may be straight or branched where the number of carbon atoms allows. $S(O)_n$alkyl and alkoxy groups incorporate such alkyl moieties. Halo means fluoro, chloro, bromo or iodo.

Pharmaceutically-, agriculturally or veterinarily-acceptable salts are well-known in the art and include, for example those mentioned by Berge et al in *J.Pharm.Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, gluconate, lactate, salicylate, citrate, tartrate, ascorbate, succinate, maleate, fumarate, formate, benzoate, methanesulphonate, ethanesulphonate, benzenesulphonate and p-toluenesulphonate salts.

Solvates (e.g. hydrates) are generally well-known in the art and can be prepared by standard methods.

Preferably the "ABNEC" ring moiety in the compound of formula (I) above is a pyrrol-1-yl, 1,2,3-triazol-1-yl, 1,2,4-triazol-1-yl, imidazol-1-yl or indol-1-yl moiety.

Preferably $R^5$ is H, $C_{1-4}$ alkyl optionally substituted by one or more halo, CN,
or when B is $CR^6$, together with the carbon atom to which it is attached and $CR^6$, is a benzo- or pyridino-ring, which benzo- or pyridino-ring is optionally substituted by one or two halo groups, and, when the pyridino-ring is present, oxide on the nitrogen of said pyridino-ring.
More preferably $R^5$ is H, CN, $CH_3$ or $CF_3$,
or when B is $CR^6$, together with the carbon atom to which it is attached and $CR^6$, is a benzo- or pyridino-ring, which benzo- or pyridino-ring is optionally substituted by one or two fluoro groups, and, when the pyridino-ring is present, oxide on the nitrogen of said pyridino-ring.
Most preferably $R^5$ is H, $CH_3$ or CN.

Preferably $R^6$ is H, halo, $C_{1-4}$ alkyl optionally substituted by one or more halo, or when A is $CR^5$, together with the carbon atom to which it is attached and $CR^5$, is a benzo- or pyridino-ring, which benzo- or pyridino-ring is optionally substituted by one or two halo groups, and, when the pyridino-ring is present, oxide on the nitrogen of said pyridino-ring.

More preferably $R^6$ is H, halo, $CH_3$ or $CF_3$, or when A is $CR^5$, together with the carbon atom to which it is attached and $CR^5$, is a benzo- or pyridino-ring, which benzo- or pyridino-ring is optionally substituted by one or two fluoro groups, and, when the pyridino-ring is present, oxide on the nitrogen of said pyridino-ring.

Most preferably, $R^6$ is H, Cl, Br or $CH_3$.

Preferably $R^1$ is a furan-2-yl, furan-3-yl, thien-2-yl, thien-3-yl or isoxazol-5-yl group, each optionally substituted by one or two substituents independently selected from halo, $C_{1-4}$ alkyl optionally substituted by one or more halo, and ($C_{1-4}$ alkyl optionally substituted by one or more halo)$S(O)_n$, or $R^1$ is a group of formula (II)

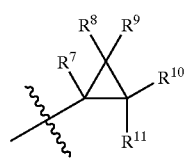

(II)

wherein $R^7$ is H or $C_{1-4}$ alkyl optionally substituted by one or more halo, $R^8$ and $R^9$ are each independently selected from H, chloro, fluoro or bromo, and $R^{10}$ and $R^{11}$ are both H.

More preferably $R^1$ is furan-2-yl, furan-3-yl, thien-2-yl, thien-3-yl or isoxazol-5-yl group, each optionally substituted by one or two substituents independently selected from fluoro, chloro, bromo, $CF_3$ and $CH_3$, or $R^1$ is a group of formula (II)

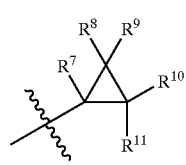

(II)

wherein $R^7$ is H, $CH_3$ or $CF_3$, $R^8$ and $R^9$ are each independently selected from H, chloro, fluoro or bromo, and $R^{10}$ and $R^{11}$ are both H.

Most preferably, $R^1$ is 3-bromisoxazol-5-yl, 2,2-dibromocyclopropyl, 2,2-dichlorocyclopropyl or 1-trifluoromethylcyclopropyl.

Preferably $R^2$ is H, $NH_2$, halo or $NHCH_2$(phenyl optionally substituted by $C_{1-4}$ alkoxy).

More preferably $R^2$ is H, $NH_2$, F, Cl or Br.

Most preferably $R^2$ is H or $NH_2$.

Preferably X is C—F, C—Cl or C—Br.

More preferably X is C—Cl.

Preferably $R^3$ is chloro.

Preferably $R^4$ is methyl optionally substituted by one or more halo, methoxy optionally substituted by one or more halo, $S(O)_n$(methyl optionally substituted by one or more halo), halo or $SF_5$.

More preferably $R^4$ is $CF_3$, $OCF_3$, $SCF_3$ or $SF_5$.

The most preferred substances are those of the Examples below, and the salts and solvates thereof.

The compounds of the formula (I) may possess one or more asymmetric centres and so exist in two or more stereoisomeric forms. The present invention includes all the individual stereoisomers of the compounds of formula (I), salts, solvates and mixtures thereof.

Separation of diastereomers may be achieved by conventional techniques, e.g. by fractional crystallisation, chromatography such as H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The substances provided by the invention can be prepared by adaptation of methods disclosed in the art, specifically in the art relating to antiparasitic pyrazoles, such as in copending International Patent Application publication number WO98/24767 and European Patent Application publication number EP 0 846 686 A1, for instance by the methods specifically described in the Examples and Preparations section below, and suitable adaptation thereof. The synthetic chemist skilled in the art will be aware of many transformations that can be used to construct the substances of the invention.

Exemplary synthetic methods are described below. In these methods the definitions for the various groups and substituents are as given above for compounds of formula (I), unless specified otherwise.

Method 1

Compounds of the formula (I) wherein $R^1$ is a group of formula (II)

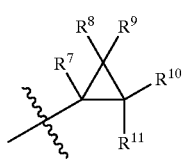

(II)

can be made from the corresponding olefinic compound of formula (III) or (IV) below by a reaction which is formally regarded as a carbene transfer or insertion reaction of a "$R^8R^9C$:" or "$R^{10}R^{11}C$:" moiety as required.

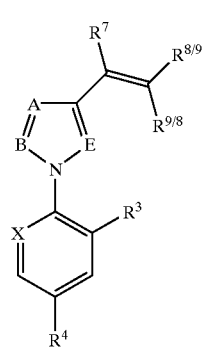

(III)

-continued

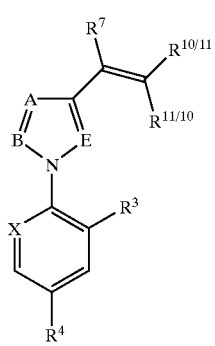

(IV)

Compounds of formulae (III) and (IV) can be made by conventional methods, for example by adaptation of the methods described for the corresponding pyrazole-4-olefins in International Patent Application publication number WO97/07102, which is herein incorporated by reference.

The carbene transfer/insertion reactions can be carried out by the methods described in various texts known in the art, such as "Carbenes, Nitrenes and Arynes" by T L Gilchrist and C W Rees, published by Nelson (1973), and "Advanced Organic Chemistry" by J March, 3rd edition, published by Wiley-Interscience (1985) (e.g. section 5–49 on pp 768–774), both of which are herein incorporated by reference. The "$R^8R^9C$:" and "$R^{10}R^{11}C$:" moieties may be generated from suitable precursors known in the art.

Method 2

Compounds of formula (I) wherein $R^1$ is a 5-membered heteroaryl group selected from furan-2-yl, furan-3-yl, thien-2-yl, thien-3-yl and isoxazol-5-yl, each of which is optionally substituted by one or two substituents independently selected from halo, $CH_3$, $CF_3$, and $CF_3S(O)_n$, can be prepared by cross-coupling reactions, for example palladium-catalysed cross-coupling, of compounds of the formula (V):

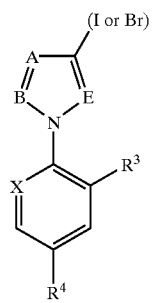

(V)

with boronic acids of the formula $ArB(OH)_2$, where Ar is a 5-membered heteroaryl group selected from furan-2-yl, furan-3-yl, thien-2-yl, thien-3-yl and isoxazol-5-yl, each of which is optionally substituted by one or two substituents independently selected from halo, $CH_3$, $CF_3$, and $CF_3S(O)_n$. The reaction is carried out using a suitable palladium (0) species such as $Pd(PPh_3)_4$, in a suitable solvent or solvent system such as N,N-dimethylformamide (DMF), ethanol/toluene/water, diglyme/water or dioxane/water, and using a suitable base such as $NaHCO_3$ or $K_2CO_3$. The general palladium-catalysed cross coupling chemistry is described by AR Martin and Y Yang in *Acta Chemica Scandinavica* (1993), 47, 221–230.

Intermediates of formula (V) above can be made by reaction of compounds of formula (VI)

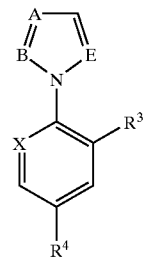

(VI)

with an iodinating or brominating species such as N-iodo- or N-bromosuccinimide in a suitable solvent such as acetonitrile.

Compounds of formula (VI) can be made by conventional methods and by suitable adaptation of the methods described later in the Examples and Preparations section.

Boronic acids of the formula $ArB(OH)_2$, where Ar is as defined above, can be made by conventional methods.

Method 3

Compounds of formula (I) where $R^1$ is 3-bromoisoxazol-5-yl can be made by reaction of compounds of the formula (VII):

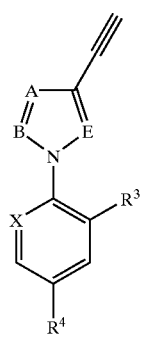

(VII)

with dibromoformaldoxime and a suitable base such as $KHCO_3$, in a suitable solvent or solvent system such as water ethyl acetate.

Compounds of formula (VII) can be made by conventional methods and those described in the Examples and Preparations section and suitable adaptation thereof, and also as described for the corresponding pyrazole-4-alkynes in International Patent Application publication no. WO 97/07102, herein incorporated by reference.

Method 4

Compounds of the formula (I) where $R^1$ is 3-(iodo, bromo, or chloro)furan-2-yl can be made according to the reaction sequence shown below:

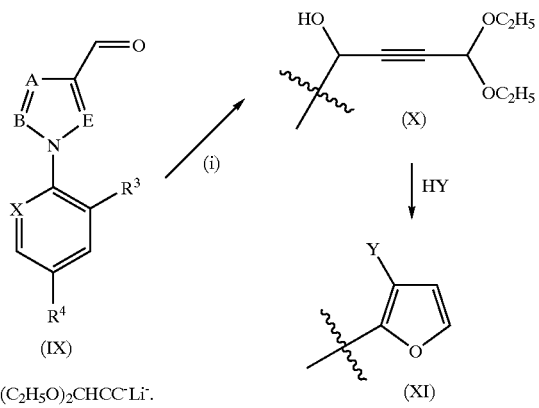

(i) $(C_2H_5O)_2CHCC^-Li^+$.

Compounds of formula (IX) can be made by oxidation of olefins of formula (III) or (IV) above where $R^7$ is H, with a suitable oxidising regime such as with osmium tetroxide/N-methylmorpholine oxide (NMMO)/sodium metaperiodate. The reaction is carried out in a suitable solvent or solvent system such as acetone/water.

Compounds of formula (X) can be made by reaction of aldehydes (IX) with the lithium salt of propiolaldehyde diethyl acetal. Preferably the lithium salt of propiolaldehyde diethyl acetal is prepared in situ from propiolaldehyde diethyl acetal and a suitable lithiating agent such as n-butyllithium. The reaction is preferably carried out in an ether solvent such as tetrahydrofuran, and preferably under an inert atmosphere such as under dry nitrogen.

Compounds of formula (XI) where Y is chloro, bromo or iodo, can be made by reaction of compounds of formula (X) with an acid such as aqueous hydro(chloric, bromic or iodic) acid. The reaction can be carried out in a suitable solvent such as dioxane. The cyclisation reaction is derived from those described by Obrecht in *Helv.Chim.Acta*, vol.72 (1989) 447.

Method 5

Compounds of the formula (I) where $R^1$ is 5-(iodo, bromo or chloro)thien-2-yl can be made by reacting the corresponding compound of formula (I) where $R^1$ is thien-2-yl (preparable by Method 2) with an iodinating, brominating or chlorinating species respectively such as the corresponding N-(iodo, bromo, or chloro)succinimide in a suitable solvent such as acetonitrile.

Method 6

Compounds of the formula (I) where $R^1$ is 5-trifluoromethylsulphenylthien-2-yl can be made by reacting the corresponding compound of formula (I) where $R^1$ is thien-2-yl (preparable by Method 2) with trifluoromethylsulphenyl chloride and stannic chloride in a suitable solvent such as dichloromethane.

Method 7

Compounds of the formula (I) where $R^1$ is 3-(iodo, bromo, or chloro)-4-(iodo, bromo, or chloro)-isoxazol-5-yl can be made by reacting the corresponding compound of formula (I) where $R^1$ is 3-(iodo, bromo, or chloro)-isoxazol-5-yl (preparable by Methods above) with an iodinating, brominating or chlorinating species respectively such as the corresponding N-(iodo, bromo, or chloro)succinimide in a suitable solvent such as acetonitrile.

Method 8

Compounds of the formula (I) where $R^1$ is 2-trifluoromethylfuran-3-yl can be made by reacting the corresponding compound of formula (I) where $R^1$ is furan-3-yl (preparable by Method 2) with $CF_3$-Z where Z is a suitable leaving group such as Br, I, Cl, etc. with sodium dithionite and disodium hydrogen phosphate in a suitable solvent such as DMF, under elevated pressure such as 1.37 bar to 3.1 bar (20 to 45 p.s.i.). This type of reaction is described in *J.Chem.Soc.*, Perkin Transactions 2, (1990) 2293.

$CF_3$-Z compounds can be made by conventional methods.

Method 9

Compounds of the formula (I) where $R^1$ is 2-(chloro or bromo)furan-3-yl can be made by reacting the corresponding compound of formula (I) where $R^1$ is furan-3-yl (preparable by Method 1) with chlorinating or brominating agents such as N-(chloro or bromo)succinimide, as appropriate, in a suitable solvent such as acetonitrile.

Method 10

Compounds of the formula (I) where $R^1$ is 2-trifluoromethylsulphenylfuran-3-yl can be made by reacting the corresponding compound of formula (I) where $R^1$ is furan-3-yl (preparable by Method 2) with with trifluoromethylsulphenyl chloride and stannic chloride in a suitable solvent such as dichloromethane.

Method 11

Compounds of the formula (I) where E is CH can be made by reacting the corresponding compound where E is $CNH_2$ with a suitable alkyl nitrite such as t-butyl nitrite, in a suitable solvent such as tetrahydrofuran (THF).

Method 12

Compounds of the formula (I) where E is C-halo can be made by reacting reacting the corresponding compound where E is $CNH_2$ with a suitable alkyl nitrite such as t-butyl nitrite, and a halide source such as iodine, tribromomethane or $CuCl_2$, in a suitable solvent such as tetrahydrofuran (THF).

Method 13

Compounds of the formula (I) where E is $C-C_{1-6}$ alkyl and $R^1$, Ar, $R^3$, $R^4$, $R^5$, $R^6$ and $R^7$ are as defined before for compounds of formula (I), can be made by reacting the corresponding compound where E is C-iodo with a lithiating species such as n-butyllithium, to make the corresponding 5-lithiated pyrazole, followed by reaction with an alkylating species ($C_{1-6}$ alkyl-Z) where Z is a suitable leaving group such as iodide or bromide.

The substances of the invention may be separated and purified by conventional methods.

It will be apparent to those skilled in the art that sensitive functional groups may need to be protected and deprotected during synthesis of substances of the invention. This may be achieved by conventional techniques, for example as described in "Protective Groups in Organic Synthesis" by T W Greene and P G M Wuts, John Wiley and Sons Inc, 1991.

The substances of the invention are useful because they possess parasiticidal activity in humans, animals and plants. They are particularly useful in the treatment of ectoparasites.

With regard to the use of the substances of the invention in humans, there is provided:

a) a pharmaceutical formulation comprising a substance of the invention in admixture with a pharmaceutically acceptable adjuvant, diluent or carrier which may be adapted for topical administration;

b) a substance of the invention, for use as a medicament;

c) the use of a substance of the invention in the manufacture of a parasiticidal medicament; and d) a method of treating a parasitic infestation in a patient which comprises administering an effective amount of a substance of the invention to the patient.

With regard to the use of the substances of the invention in non-human animals, the substances may be administered alone or in a formulation appropriate to the specific use envisaged and to the particular species of host animal being treated and the parasite involved. The methods by which the substances may be administered include oral administration by capsule, bolus, tablet or drench, or as a pour-on or spot-on formulation, or alternatively, they can be administered by injection (e.g. subcutaneously, intramuscularly or intravenously), dip, spray, mousse, shampoo, powder, or as an implant.

Such formulations are prepared in a conventional manner in accordance with standard veterinary practice. Thus capsules, boluses or tablets may be prepared by mixing the active substance with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier such that the final formulation contains from, for instance, 0.01 to 10% by weight of the active ingredient.

These formulations will vary with regard to the weight of active substance contained therein depending on the species of host animal to be treated, the severity and type of infection and the body weight of the host. For parenteral, topical (e.g. using pour-on or spot-on, dip, spray, mousse, shampoo or powder to deliver the compound) and oral administration, typical dose ranges of the active ingredient are 0.01–100 mg per kg of body weight of the animal. Preferably the range is 0.1 to 10 mg per kg.

As an alternative the substances of the invention may be administered with the animal feedstuff and for this purpose a concentrated feed additive or premix may be prepared for mixing with the normal animal feed.

The substances of the invention have utility in the control of arthropod, plant nematode, helminth or protozoan pests. The substances of the invention may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fish, for example Acarina, including ticks (e.g. *Ixodes* spp., *Boophilus* spp. e.g. *Boophilus microplus, Amblyomma* spp., *Hyalomma* spp., *Rhipicephalus* spp. e.g. *Rhipicephalus appendiculatus, Haemaphysalis* spp., *Dermacentor* spp., *Omithodorus* spp. (e.g. *Ornithodorus moubata* and mites (e.g. *Damalinia* spp., *Dermahyssus gallinae, Sarcoptes* spp. e.g. *Sarcoptes scabiei, Psoroptes* spp., *Chorioptes* spp., *Demodex* spp., *Eutrombicula* spp.,) *Diptera* (e.g. *Aedes* spp., *Anopheles* spp., *Musca* spp., *Hypoderma* spp., *Gastrophilus* spp., *Simulium* spp.); Hemiptera (e.g. *Triatoma* spp.); Phthiraptera (e.g. *Damalinia* spp., *Linoqnathus* spp.) Siphonaptera (e.g. *Ctenocephalides* spp.); Dictyoptera (e.g. *Periplaneta* spp., *Blatella* spp.); Hymenoptera (e.g. *Monomorium pharaonis*); for example against infections of the gastrointestinal tract caused by parasitic nematode worms, for example members of the family Trichostrongylidae, *Nippostronylus brasiliensis, Trichinella spiralis, Haemonchus contortus, Trichostronylus colubriformis, Nematodirus battus, Ostertagia circumcincta, Trichostrongylus axei, Cooperia* spp. and *Hymenolepis nana*, in the control and treatment of protozoal diseases caused by, for example *Eimeria* spp. e.g. *Eimeria tenella, Eimeria acervulina, Eimeria brunetti, Eimeria maxima, Eimeria necatrix, Eimeria bovis, Eimeria zuerni* and *Eimeria ovinoidalis; Trypanosoma cruzi, Leishmania* spp., *Plasmodium* spp., *Babesia* spp., *Trichomonadidae* spp., *Histomonas* spp., *Giardia* spp., *Toxoplasma* spp., *Entamoeba histolytica* and *Theileria* spp.; in the protection of stored products, for example cereals, including grain and flour, groundnuts, animal foodstuffs, timber and household goods, e.g. carpets and textiles, against attack by arthropods, more especially beetles, including weevils, moths and mites, for example *Ephestia* spp. (flour moths), *Anthrenus* spp. (carpet beetles), *Tribolium* spp. (flour beetles), *Sitophilus* spp. (grain weevils) and *Acarus* spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, *Reticulitermes* spp., *Heterotermes* spp., *Coptoterms* spp.; in agriculture, against adults, larvae and eggs of Lepidoptera (butterflies and moths), e.g. *Heliothis* spp. such as *Heliothis virescens* (tobacco budworm), *Heliothis armioera* and *Heliothis zea, Spodoptera* spp. such as *S. exempta, S. littoralis* (Egyptian cotton worm), *S. eridania* (southern army worm), *Mamestra configurata* (bertha army worm); *Earias* spp. e.g. *E. insulana* (Egyptian bollworm), *Pectinophora* spp. e.g. *Pectinophora gossypiella* (pink bollworm), *Ostrinia* spp. such as *O. nubilalis* (European cornborer), *Trichoplusia ni* (cabbage looper), *Pieris* spp. (cabbage worms), *Laphyqma* spp. (army worms), *Agrotis* and *Amathes* spp. (cutworms), *Wiseana* spp. (porina moth), *Chilo* spp. (rice stem borer), *Tryporyza* spp. and *Diatraea* spp. (sugar cane borers and rice borers). *Sparganothis pilleriana* (grape berry moth), *Cydia pomonella* (codling moth), *Archips* spp. (fruit tree tortrix moths), *Plutella xylostella* (diamond black moth); against adult and larvae of Coleoptera (beetles) e.g. *Hypothenemus hampei* (coffee berry borer), *Hylesinus* spp. (bark beetles), *Anthonomus grandis* (cotton boll weevil), *Acalymma* spp. (cucumber beetles), *Lema* spp., *Psylliodes* spp., *Leptinotarsa decemlineata* (Colorado potato beetle), *Diabrotica* spp. (corn rootworms), *Gonocephalum* spp. (false wire worms),; *Agriotes* spp. (wireworms), *Dermolepida* and *Heteronychus* spp. (white grubs), *Phaedon cochleariae* (mustard beetle), *Lissorhoptrus oryzophilus* (rice water weevil), *Melioethes* spp. (pollen beetles), *Ceutorhynchus* spp., *Rhynchophorus* and *Cosmopolites* spp. (root weevils); against Hemiptera e.g. *Psylla* spp., *Bemisia* spp., *Trialeurodes* spp., *Aphis* spp., *Myzus* spp., *Megoura viciae, Phylloxera* spp., *Adelges* spp., *Phorodon humuli* (hop damson aphid), *Aeneolamia* spp., *Nephotettix* spp. (rice leaf hoppers), *Empoasca* spp., *Nilaparvata* spp., *Perkinsiella* spp., *Pyrilla* spp., *Aonidiella* spp. (red scales), *Coccus* spp., *Pseucoccus* spp., *Helopeltis* spp. (mosquito bugs), *Lygus* spp., *Dysdercus* spp., *Oxycarenus* spp., *Nezara* spp.; Nymenoptera e.g. *Athalia* spp. and *Cephus* spp. (saw flies), *Atta* spp. (leaf cutting ants); Diptera e.g. *Hylemyia* spp. (root flies), *Atherigona* spp. and *Chlorops* spp. (shoot flies), *Phytomyza* spp. (leaf miners), *Ceratitis* spp. (fruit flies); Thysanoptera such as *Thrips tabaci*:Orthoptera such as *Locusta* and *Schistocerca* spp. (locusts) and crickets e.g. *Gryllus* spp. and *Acheta* spp.; Collembola e.g.

*Sminthurus* spp. and *Onychiurus* spp. (springtails), Isoptera e.g. *Odontotermes* spp. (termites), Dermaptera e.g. *Forficula* spp. (earwigs) and also other arthropods of agricultural significance such as Acari (mites) e.g. *Tetranychus* spp., *Panonychus* spp. and *Bryobia* spp. (spider mites), *Eriophyes* spp. (gall mites), *Polyphacotarsonemus* spp.; *Blaniulus* spp. (millipedes), *Scutigerella* spp. (symphilids), *Oniscus* spp. (woodlice) and *Triops* spp. (crustacea); nematodes which attack plants and trees of importance to agriculture, forestry and horticulture either directly or by spreading bacterial, viral, mycoplasma or fungal diseases of the plants, root-knot nematodes such as *Meliodogyne* spp. (e.g. *M. incognita*); cyst nematodes such as *Globodera* spp. (e.g. *G. rostochiensis*); *Heterodera* spp. (e.g. *H. avenae*); *Radopholus* spp. (e.g. *R. similis*); lesion nematodes such as *Pratylenchus* spp. (e.g. *P. pratensis*); *Belonoliamus* spp. (e.g. *B. gracilis*); *Tylenchulus* spp. (e.g. *T. semipenetrans*); *Rotylenchulus* spp. (e.g. *R. reniformis*); *Rotylenchus* spp. (e.g. *R. robustus*); *Helicotylenchus* spp. (e.g. *H. multicinctus*); *Hemicycliophora* spp. (e.g. *H. gracilis*); *Criconemoides* spp. (e.g. *C. similis*); *Trichodorus* spp. (e.g. *T. primitivus*); dagger nematodes such as *Xiphinema* spp. (e.g. *X. diversicaudatum*), *Longidorus* spp. (e.g. *L. elongatus*); *Hoplolaimus* spp. (e.g. *H. coronatus*); *Aphelenchoides* spp. (e.g. *A. ritzema-bosi. A. besseyi*); stem and bulb eelworms such as *Ditylenchus* spp. (e.g. *D. dipsaci*).

The substances of the invention also have utility in the control of arthropod or nematode pests of plants. The active substance is generally applied to the locus in which arthropod or nematode infestation is to be controlled at a rate of about 0.005 kg to about 25 kg of active compound per hectare of locus treated, preferably 0.02 to 2 kg/ha. Under ideal conditions, depending on the pest to be controlled, the lower rate may offer adequate protection. On the other hand, adverse weather conditions, resistance of the pest and other factors may require that the active ingredient be used in higher proportions. For foliar application, a rate of 0.01 to 1 kg/ha may be used.

When the pest is soil-borne, the formulation containing the active substance is distributed evenly over the area to be treated in any convenient manner. Application may be made, if desired, to the field or crop-growing area generally or in close proximity to the seed or plant to be protected from attack. The active substance can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The substances of the invention may be applied in solid or liquid compositions to the soil principally to control those nematodes dwelling therein but also to the foliage principally to control those nematodes attacking the aerial parts of the plants (e.g. *Aphelenchoides* spp. and *Ditylenchus* spp. listed above).

The substances of the invention are of value in controlling pests which feed on parts of the plant remote from the point of application, e.g. leaf feeding insects are killed by the subject substances applied to roots. In addition the substances may reduce attacks on the plant by means of antifeeding or repellent effects.

The substances of the invention are of particular value in the protection of field, forage, plantation, glasshouse, orchard and vineyard crops, or ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids), or termites, for example, *Reticulitermes* spp., *Heterotermes* spp., *Coptotermes* spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The substances of the invention are of value in the control of arthropods, helminths or protozoa which are injurious to, or spread or act as vectors of diseases in man and other animals, e.g. domestic animals, such as those hereinbefore mentioned, and more especially in the control of ticks, mites, lice, fleas, midges and biting, nuisance and myiasis flies. The substances of the invention are also useful in controlling arthropods, helminths or protozoa which are present, for example, inside domestic host animals or which feed in or on the skin or suck the blood of the animal, for which purpose they may be administered orally, parenterally, percutaneously or topically.

According to a further aspect of the invention, there is provided a parasiticidal formulation comprising a substance of the invention, in admixture with a compatible adjuvant, diluent or carrier. Preferably, the formulation is adapted for topical administration.

The invention further provides a substance of the invention for use as a parasiticide; and a method of treating a parasitic infestation at a locus, which comprises treatment of the locus with an effective amount of a substance of the invention. Preferably, the locus is the skin or fur of an animal, or a plant surface or the soil around the plant to be treated.

The invention further provides:

the processes described herein for preparing the compounds of formula (I) and salts and solvates thereof;

pharmaceutical, veterinary or agricultural parasiticidal formulations comprising a compound of formula (I), or a pharmaceutically-, agriculturally- or veterinarily-acceptable salt and/or solvate thereof, in admixture with a compatible adjuvant, diluent or carrier;

compounds of formula (I), and pharmaceutically- or veterinarily-acceptable salts and/or solvates, and formulations thereof, for use as a medicament;

the use of a compound of formula (I), or pharmaceutically- or veterinarily-acceptable salt therof, or formulation thereof, in the manufacture of a medicament for the treatment of a parasitic infestation;

a method of killing or harming a parasite at a locus; and any novel intermediates described herein.

It is to be appreciated that reference to treatment herein includes prophylaxis as well as the alleviation of established symptoms of a condition, such as a parasitic infection.

Test for Insecticidal Activity

Adult flies (*Stomoxys calcitrans*) are collected and anaesthetized using $CO_2$, 1 μl of an acetone solution containing the test substance is applied directly to the thorax of the fly. The flies are then placed carefully into a 50 ml tube covered with damp gauze to recover from the $CO_2$. Negative controls have 1 μl of acetone dispensed onto them. Mortality is assessed 24 hours after dosing. The table below illustrates the in vivo activity of a selection of the substances of the invention against such flies. Dosages required to produce 100% mortality are expressed in μg/fly.

| Example No. | Dosage |
|---|---|
| 1 | 0.005 |
| 2 | 0.01 |
| 3 | 0.005 |
| 4 | 0.05 |
| 6 | 0.01 |

Test for Acaricidal Activity

A dose of 10 μg/cm$^2$ is created by evenly pipetting 0.5 ml of a 1 mg/ml solution of the test compound in a suitable solvent such as acetone or ethanol onto a Whatman No. 1 (Trade Mark) filter paper cut to a size of 8×6.25 cm. When dry, the paper is folded in half, sealed on two sides using a crimping device and placed in a Kilner jar containing a cotton wool pad dampened with water. The jar is then sealed and placed at 25° C. for 24 hours. Next, approximately 50 *Boophilus microplus* larvae are introduced into the treated paper envelope which is then crimped along the third side to effect a complete seal. The paper envelope is returned to the Kilner jar, which is sealed and placed at 25° C. for a further 48 hours. The papers are then removed and mortality assessed. Negative controls are provided by treating an appropriately cut filter paper with 0.5 ml of solvent only and following the same procedure. Activity at other doses is obtained by varying the concentration of the test solution. The table below illustrates the in vivo activity of a selection of the compounds of the invention against *Boophilus microplus* larvae. Dosages are expressed in μg/cm$^2$.

| Example No. | Dosage/% Mortality | |
|---|---|---|
| 1 | 0.5 | 90% |
| 2 | 1 | 100% |
| 3 | 0.5 | 100% |

The invention is illustrated by the following Examples. In the Examples and Preparations, melting points were determined using a Gallenkamp melting point apparatus and are uncorrected. Nuclear magnetic resonance (NMR) data were obtained using a Bruker AC300 or AM300 and are quoted in parts per million using solvent or tetramethylsilane as reference. Mass spectral (MS) data were obtained on a Finnigan Mat. TSQ 7000 or a Fisons Instruments Trio 1000. The calculated and observed ions quoted refer to the isotopic composition of lowest mass. HPLC purification was performed on a 21×250 mm Dynamax™ 5 μODS reverse-phase column eluted at 10 ml/minute with acetonitrile:0.005M aqueous heptanesulphonic acid:methanol (50:40:10). Fractions were processed by evaporation of the non-aqueous components followed by partition between ether and saturated aqueous sodium hydrogen carbonate solution. The organic layer was then separated, dried and evaporated.

EXAMPLES

Example 1

4-(2,2-Dibromocyclopropyl)-1-(2,6-dichloro-4-trifluoromethylphenyl)-1,2,3-triazole To a solution of the title compound of Preparation 2 (210 mg) in bromoform (4 ml) and dichloromethane (2 ml) was added sodium hydroxide (200 mg in water (0.2 ml)) and benzyltriethylammonium chloride (10 mg), the mixture was stirred vigourously for 16 hours at room temperature. Further equivalents of sodium hydroxide (200 mg in water (0.2 ml)) and benzyltriethylammonium chloride (10 mg) were added to the reaction, which was stirred for a further 4 days. The reaction was diluted with water (100 ml) and extracted with dichloromethane (100 ml), the organic layer was separated, evaporated to dryness and purified by column chromatography on silica gel (5 g) eluted with dichloromethane hexane (3:1) to give the title compound as a yellow crystaline solid, m.p. 156–158° C.

$\delta(CDCl_3)$: 7.76 (2H,s), 7.20 (1H,s), 2.88 (1H,dd), 2.20 (1H,dd), 1.94 (1H,dd). MS (thermospray): M/Z [M+NH$_4$] 497.9; $C_{12}H_6Br_2Cl_2F_3N_3$+NH$_4$ requires 498.0.

Example 2

4-(2,2-Dichlorocyclopropyl)-1-(2,6-dichloro-4-trifluoromethylphenyl)-1,2,3-triazole To a solution of the title compound of Preparation 2 (200 mg) in toluene (5 ml) was added phenyl(trichloromethyl) mercury (309 mg). The mixture was heated to 70° C. for 6 hours and then left to stir for 16 hours at room temperature. A further mole equivalent of phenyl(trichloromethyl) mercury (309 mg) was added, the reaction was heated to 100° C. for 8 hours and then left to stir for 16 hours at room temperature. The reaction was diluted with water (100 ml) and extracted with dichloromethane (100 ml), the organic fraction was separated, evaporated to dryness and purified by column chromatography on silica gel (20 g) eluted with dichloromethane to give the title compound as a pale yellow crystaline solid, m.p. 134–136° C.

$\delta(CDCl_3)$: 7.78 (2H,s), 7.18 (1H,s), 3.03 (1H,t), 2.20 (2H,d). MS (thermospray): M/Z [M+NH$_4$] 407.2; $C_{12}H_6Cl_4F_3N_3$+NH$_4$ requires 407.0.

Example 3

3-Cyano-4-(2,2-dibromocyclopropyl)-1-(2,6-dichloro-4-trifluoromethylphenyl)pyrrole To a solution of the title compound of Preparation 5 (200 mg) in bromoform (1 ml), dichloromethane (0.5 ml) and ethanol (0.1 ml) was added sodium hydroxide (100 mg in $H_2O$ (0.1 ml)) and benzyltriethylammonium chloride (5 mg), the mixture was stirred vigourously for 3 days at room temperature. The reaction was diluted with water (100 ml) and extracted with ether (100 ml), the organic fraction was separated, dried over MgSO$_4$, filtered, evaporated to dryness and purified by reverse phase HPLC on C18 silica using acetonitrile:water:methanol (60:30:10) as eluent, to give the title compound as a colourless gum-like solid.

$\delta(CDCl_3)$: 7.78 (2H,s), 7.18 (1H,s), 6.56 (1H,s), 2.88 (1H,dd), 2.24 (1H,dd), 1.94 (1H,dd). MS (thermospray): M/Z [M+NH$_4$] 517.9; $C_{15}H_7Br_2Cl_2F_3N_2$+NH$_4$ requires 517.9.

Example 4
3-(2,2-Dibromocyclopropyl)-1-(2,6-dichloro-4-trifluoromethylphenyl)indole To a solution of the title compound of Preparation 7 (200 mg) in bromoform (4 ml) and dichloromethane (2 ml) was added sodium hydroxide (200 mg in H$_2$O (0.2 ml)) and benzyltriethylammonium chloride (10 mg). The mixture was stirred vigourously for 16 hours at room temperature. The reaction was diluted with water (100 ml) and extracted with dichloromethane (100 ml), the organic fraction was separated, dried over MgSO$_4$, filtered and evaporated to dryness. The residue was purified by column chromatography on silica gel (20 g) eluted with dichloromethane:hexane (1:5) to give the title compound as a colourless gum-like solid. δ(CDCl$_3$): 7.72–7.90 (3H,m), 7.20–7.30 (2H,m), 6.92 (1H,d), 6.84 (1H,s), 3.02 (1H,dd), 2.12 (1H,dd), 1.94 (1H, dd). M/Z [M+NH$_4$] 545.8; C$_{18}$H$_{10}$Br$_2$Cl$_2$F$_3$N+NH$_4$ requires 546.0

Example 5
3-(2,2-Dibromocyclopropyl)-1-(2,6-dichloro-4-trifluoromethylphenyl)-6-fluoroindole To a solution of the title compound of Preparation 10 (20 g) in bromoform (80 ml), dichloromethane (400 ml) and ethanol (20 ml) was added sodium hydroxide (40 g in H$_2$O (40 ml)) and benzyltriethylammonium chloride (0.80 g). The mixture was heated under reflux for 6 hours and then stirred for a further 48 hours at room temperature. The reaction was diluted with water (1000 ml) and extracted with dichloromethane (1000 ml), the organic fraction was separated, dried over MgSO$_4$, filtered and evaporated to dryness. The residue was purified by column chromatography on silica gel (1 kg) eluted with dichloromethane to give the title compound as a colourless gum-like solid. δ(CDCl$_3$): 7.70–8.00 (3H,m), 6.98–7.16 (1H,m), 6.80–6.94 (1H,m), 6.50–6.70 (1H,m), 2.98 (1H,dd), 2.24 (1H,dd), 1.94 (1H,dd).

Example 6
3-(2,2-Dibromocyclopropyl)-1-(2,6-dichloro-4-trifluoromethylphenyl)-1,2,4-triazole To a solution of the title compound of Preparation 13 (600 mg) in bromoform (20 ml) and dichloromethane (20 ml) was added sodium hydroxide (400 mg in 0.4 ml H$_2$O) and benzyltriethylammonium chloride (100 mg), the mixture was stirred vigourously for 3 days at room temperature. The reaction was diluted with water (100 ml) and extracted with dichloromethane (100 ml), the organic fraction was separated, dried over MgSO$_4$, filtered, evaporated to dryness and purified by column chromatography on silica gel (20 g) eluted with dichloromethane to give the title compound as a yellow gum-like solid.

δ(CDCl$_3$): 8.18 (1H,s), 7.76 (2H,s), 3.10 (1H,dd), 2.42 (1H,dd), 2.10 (1H,dd). MS (thermospray): M/Z [M+H] 478.3:C$_{12}$H$_6$Br$_2$Cl$_2$F$_3$N$_3$+H requires 477.8.

Example 7
4-(3-Bromoisoxazol-5-yl)-1-(2,6-dichloro-4-trifluoromethylphenyl-1,2,3-triazole To a rapidly stirred solution of the compound of Preparation 14 (1.06 g) in ethyl acetate (25 ml) and water (2.5 ml) was added potassium hydrogen carbonate (0.658 g) and dibromoformaldoxime (0.703 g) respectively. The reaction was left stirring at room temperature overnight. A further 0.703 g of dibromoformaldoxime was added and the reaction stirred for a further 5 hours. The solvent was evaporated by rotary evaporation in vacuo and the reaction mixture dissolved in methylene chloride (60 ml) and washed with water (2×50 ml). The organics were separated, dried (MgSO$_4$), filtered, evaporated to dryness and purified by column chromatography on silica gel (100 g) eluted with hexane: ethyl acetate (95:5) to give the title compound as a pale yellow solid.

δ(CDCl$_3$): 8.20 (1H,s), 7.85 (2H,s), 6.97 (1H,s).

Example 8
3-(3-Bromoisoxazol-5-yl)-1-(2,6-dichloro-4-trifluoromethylphenyl)indole To a rapidly stirred solution of the title compound of Preparation 15 (1.0 g) in ethyl acetate (25 ml) and water (2.5 ml) was added potassium hydrogen carbonate (0.54 g) and dibromoformaldoxime (1.4 g) respectively. The reaction was left stirring at room temperature overnight. The solvent was evaporated by rotary evaporation in vacuo and the reaction mixture dissolved in methylene chloride (50 ml) and washed with water (2×50 ml). The organics were separated, dried (Na$_2$SO$_4$), filtered, evaporated to dryness and purified by column chromatography on silica gel (50 g) eluted with hexane followed by dichloromethane to give the title compound as a white solid (284 mg).

δ(CDCl$_3$): 8.0 (1H,d), 7.8 (2H,s), 7.7 (1H,s), 7.3–7.5 (2H,m), 7.0 (1H,d), 6.6 (1H,s).

PREPARATIONS

Preparation 1
1-(2,6-Dichloro-4-trifluoromethylphenyl)-4-iodo-1,2,3-triazole To a solution of 1-(2,6-dichloro-4-trifluoromethylphenyl)-4-trimethylsilyl-1,2,3-triazole (EP-400842-A1; 1.00 g) in tetrahydrofuran (20 ml) was added silver trifluoroacetate (623 mg) and iodine (716 mg) at −78° C. under an atmosphere of nitrogen. The reaction was allowed to warm to room temperature over 1 hour and then left to stir for a further 16 hours. The reaction was filtered and the filtrate diluted with water (100 ml) and extracted with ether (100 ml), the organic fraction was separarted, dried over MgSO$_4$, filtered and evaporated to dryness. The residue was purified by column chromatography (silica, 100 g) eluted with dichloromethane:hexane (2:1) to give the title compound as a pale yellow crystalline material, m.p. 194–195° C.

Preparation 2
1-(2,6-Dichloro-4-trifluoromethylphenyl)-4-ethenyl-1,2,3-triazole To a solution of the title compound of Preparation 1 (500 mg) in dimethylformamide (50 ml) was added tributylvinyltin (715 μl) and tetrakis(triphenylphosphine)palladium (0) (50 mg). The reaction was heated to 100° C. under nitrogen for 1 hr, diluted with water (100 ml) and extracted with ether (100 ml), the organic fraction was separated were dried over MgSO$_4$, filtered and evaporated to dryness. The residue was purified by column chromatography (silica, 50 g) eluted with dichloromethane:hexane (3:1) to give the title compound as a white crystaline material, m.p. 109–111° C.

Preparation 3
2-Amino-4-cyano-1-(2,6-dichloro-4-trifluoromethylphenyl)-3-iodopyrrole To a solution of 2-amino-1-(2,6-dichloro-4-trifluoromethylphenyl)-4-cyanopyrrole (EP-372982 A2) in acetonitrile (20 ml) was added N-iodosuccinimide (703 mg). The reaction was stirred at room temperature for 30 minutes, diluted with water (100 ml) and extracted with ether (100 ml). The organic fraction was separated, dried over MgSO$_4$, filtered and evaporated to dryness, the residue was purified by column chromatography (silica, 20 g) eluted with dichloromethane:hexane (7:3) to give the title compound as a yellow crystaline material, m.p. 130–132° C.

Preparation 4
4-cyano-1-(2,6-dichloro-4-trifluoromethylphenyl)-3-iodopyrrole

To a solution of the title compound of Preparation 3 in tetrahydrofuran (120 ml) was added tert-butyl nitrite (4 ml). The reaction was refluxed for 1 hr and then evaporated to dryness, the residue was purified by column chromatography on silica gel (500 g) eluted with dichloromethane:hexane (7:3) to give the title compound as a pale yellow crystaline material, m.p. 118–120° C.

Preparation 5
3-Cyano-1-(2,6-dichloro-4-trifluoromethylphenyl)-4-ethenylpyrrole

To a solution of the title compound of Preparation 4 (2.50 g) in dimethylformamide (100 ml) was added tributylvinyltin (5 ml) and tetrakis(triphenylphosphine)palladium (0) (300 mg). The reaction was heated to 100° C. under nitrogen for 1 hr, and the mixture was evaporated to dryness. The residue was purified by column chromatography on silica gel (500 g) eluted with dichloromethane:hexane (7:3) to give the title compound as a white crystalline solid, m.p. 55–60° C.

Preparation 6
1-(2,6-Dichloro-4-trifluoromethylphenyl)-3-formylindole

To a solution of 3,5-dichloro-4-fluorobenzotrifluoride (1.0 g) in dimethylformamide (10 ml) was added 3-formylindole (623 mg) and potassium carbonate (593 mg), the mixture was heated at 90° C. for 1.5 hrs. The reaction was cooled to room temperature and diluted with water (200 ml) and extracted with ether (200 ml). The organic fraction was separated and evaporated to dryness to give the title compound as a pale yellow crystaline material, m.p. 167–169° C.

Preparation 7
1-(2,6-Dichloro-4-trifluoromethylphenyl)-3-ethenylindole

To a solution of methyltriphenylphosphonium bromide (714 mg) in tetrahydrofuran (20 ml) was added n-butyl lithium (0.8 ml, 2.5M in hexanes) under nitrogen at 0° C. After 10 minutes the title compound of Preparation 6 (700 mg) was added. The reaction was stirred for a further 1 hr and then poured into an iced solution of 10% ammonium chloride (50 ml), extracted with ether (100 ml) washed with brine (50 ml), dried over $MgSO_4$, filtered and evaporated an oil. The residue was purified by column chromatography on silica gel (10 g) eluted with dichloromethane:hexane (7:3) to give the title compound as a pale yellow crystalline material, m.p. 85–87° C.

Preparation 8
1-(2,6-Dichloro-4-trifluoromethylphenyl)-6-fluoroindole

To a solution of 3,5-dichloro-4-fluorobenzotrifluoride (34.5 g) in dimethylformamide (250 ml) was added 6-fluoroindole (34.5 g) and potassium carbonate (20.4 g). The mixture was heated at 90° C. for 6 hours and then left to stir for 16 hours at room temperature. The reaction was diluted with water (1000 ml) and extracted with hexane (1000 ml). The organic fraction was separated and evaporated to dryness to give the title compound as a colourless liquid.

$\delta(CDCl_3)$: 7.80 (2H,s), 7.62 (1H,dd), 7.20 (1H,d), 6.96 (1H,dt), 6.76 (1H,d), 6.62 (1H,dd).

Preparation 9
3-Bromo-1-(2,6-dichloro-4-trifluoromethylphenyl)-6-fluoroindole

To a solution of the title compound of Preparation 8 (37.8 g) in N,N-dimethylformamide (200 ml) was added bromine (6.8 ml) in N,N-dimethylformamide (200 ml) dropwise over 10 minutes, and the reaction was stirred at room temperature for 1 hour. The reaction was diluted with a solution of ammonia (10 ml) and sodium metabisulphite (2.0 g) in water (1000 ml), and extracted with hexane (2×500 ml), dried over $MgSO_4$, filtered and evaporated to give the title compound as a colourless oil.

$\delta(CDCl_3)$: 7.80 (2H,s), 7.60 (1H,dd), 7.22 (1H,s), 7.08 (1H,dt), 6.64 (1H,dd).

Preparation 10
1-(2,6-Dichloro-4-trifluoromethylphenyl)-3-ethenyl-6-fluoroindole To a solution of the title compound of Preparation 9 (44.3 g) in dimethylformamide (400 ml) was added tributylvinyltin (35 ml) and tetrakis(triphenylphosphine)palladium (0) (2.7 g). The reaction was heated to 70° C. for 24 hrs under an atmosphere of nitrogen and then left to stir at room temperature for a further 4 days, after which tetrakis(triphenylphosphine)palladium (0) (2.5 g) was added and the reaction heated to 70° C. for 24 hrs. The reaction mixture was evaporated to dryness and the residue was purified by column chromatography on silica gel (1 kg), eluted with hexane to give the title compound as a colourless oil.

$\delta(CDCl_3)$: 7.74 (1H,dd), 7.80 (2H,s), 7.22 (1H,s) 7.02 (1H,dt), 6.80 (1H,dd), 6.60 (1H,dd), 5.80 (1H,d), 5.30 (1H,d).

Preparation 11
3-Amino-1-(2,6-dichloro-4-trifluoromethylphenyl)-1,2,4-triazole;
5-Amino-1-(2,6-dichloro-4-trifluoromethylphenyl)-1,2,4-triazole (60:40 mixture)

To a solution of 3,5-dichloro-4-fluorobenzotrifluoride (1.0 g) in dimethylformamide (5 ml) was added 3-amino-1,2,4-triazole (360 mg) and potassium carbonate (296 mg), the mixture was heated at 100° C. for 2 hrs. The reaction was cooled to room temperature, diluted with water (100 ml) and extracted with ether (100 ml). The organic extracts were evaporated to dryness to give the title compounds as pale yellow crystals.

Preparation 12
1-(2,6-Dichloro-4-trifluoromethylphenyl)-3-iodo-1,2,4-triazole

To a solution of the title compounds of Preparation 11 (600 mg) in diiodomethane (4 ml) was added t-butyl nitrite (2 ml), and the reaction was stirred at room temperature for 1 hr, then diluted with water (100 ml), extracted with ether (100 ml), dried over $MgSO_4$, filtered and evaporated to an oil. The residue was purified by column chromatography (silica, 100 g) eluted with dichloromethane:hexane (10:1) to give exclusively the title compound as yellow crystals, m.p. 130–132° C.

Preparation 13
1-(2,6-Dichloro-4-trifluoromethylphenyl)-3-ethenyl-1,2,4-triazole To a solution of the title compound of Preperation 12 (204 mg) in N,N-dimethylformamide (3 ml) was added tributylvinyltin (291 ul) and tetrakis(triphenylphosphine)palladium (0) (5 mg). The reaction was heated to 90° C. under nitrogen for 5 hrs, evaporated to dryness and the residue was purified by column chromatography on silica gel (10 g) eluted with dichloromethane to give the title compound as a white crystals, m.p. 97–99° C.

Preparation 14
1-(2,6-Dichloro-4-trifluoromethylphenyl)-4-ethynyl-1,2,3-triazole To a solution of the title compound of Preparation 1 (25.02 g), trimethylsilylacetylene (260 ml) and diisopropylamine (230 ml) in tetrahydrofuran, (700 ml) was added copper (I) iodide (0.465 g) and $PdCl_2(PPh_3)_2$ (0.865 g). The reaction mixture was heated to reflux for 5 hours, evaporated to dryness and purified using column chromatography on silica gel (350 g) eluted with dichloromethane to give a brown oil. The resulting material was dissolved in tetrahydrofuran (500 ml), cooled to −78° C. and tetrabutylammonium fluoride (90.7 ml) was added dropwise. After the addition was complete the reaction was allowed to warm to room temperature, the mixture was diluted with water (250 ml), extracted with methylene chloride (400 ml), dried (MgSO$_4$), filtered, evaporated to dryness and purified by column chromatography on silica gel (400 g) eluted with dichloromethane:hexane (90:10). Recystallisation of the material in hexane yielded the title compound as a light brown solid.

δ(CDCl$_3$): 7.93 (1H,s), 7.82 (2H,s), 3.38 (1H,s).

Preparation 15

1-(2,6-Dichloro-4-trifluoromethylphenyl-3-ethynylindole

To a solution of 3,5-dichloro-4-fluorobenzotrifluoride (4.79 g) in dimethylformamide (25 ml) was added 3-ethynylindole (2.9 g) and potassium carbonate (2.84 g), the mixture was heated at 90° C. for 3 hours under an atmosphere of nitrogen and then left to stir overnight at room temperature. The reaction was diluted with water (100 ml) and extracted with hexane (2×100 ml). The organic fractions were separated, combined, evaporated to dryness and purified by column chromatography on silica gel (300 g) eluted with hexane: ethylacetate (97:3) to give the title compound as a white solid (1.3 g), m.p. 120–122° C.

δ(CDCl$_3$): 6.9–7.8 (7H,m), 3.3 (3H,s).

What is claimed is:

1. A compound of formula (I),

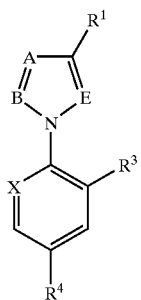

(I)

wherein A is N,

B is CR$^6$, wherein R$^6$ is selected from H, C$_{1-4}$ alkyl optionally substituted by one or more halo, CN and halo, R$^1$ is 2,2-dibromocyclopropyl, 2,2-dichlorocyclopropyl or 1-trifluoromethylcyclopropyl E is N X is CR$^{12}$, wherein R$^{12}$ is halo, R$^3$ is halo, R$^4$ is C$_{1-4}$ alkyl optionally substituted by one or more halo, C$_{1-4}$ alkoxy optionally substituted by one or more halo, S(O)$_n$(C$_{1-4}$ alkyl optionally substituted by one or more halo), halo or SF$_5$, and n is 0, 1 or 2, or a pharmaceutically-, agriculturally- or veterinarily-acceptable salts thereof, or solvate of any such compound or salt.

2. A compound, salt or solvate according to claim 1 wherein B is CR$^6$ and R$^6$ is H, halo, CH$_3$ or CF$_3$.

3. A compound, salt or solvate according to claim 1 wherein R$^3$ is chloro.

4. A compound, salt or solvate according to claim 1 wherein R$^4$ is CF$_3$, OCF$_3$, SCF$_3$ or SF$_5$.

5. A compound, salt or solvate according to claim 4 wherein B is CR$^6$ and R$^6$ is H, Cl, Br or CH$_3$.

6. A compound, salt or solvate according to claims 1, 3, 4 or 5 wherein X is C—Cl.

7. A compound selected from:

3-(2,2-dibromocyclopropyl)-1-(2,6-dichloro-4-trifluoromethylphenyl)-1,2,4-triazole; or a salt or solvate thereof.

8. A pharmaceutical or veterinary formulation comprising a substance according to claims 1, 3, 4, 5 or 7 and a compatible acceptable adjuvant, carrier or carrier.

9. A formulation according to claim 8 which is adapted for topical administration.

10. A method of treating a parasitic infestation at a locus, for example in an animal patient, which comprises administering an effective amount of a substance according to claims 1, 3, 4, 5 or 7 to the locus.

11. A method of killing or harming a parasite at a locus comprising administration of a substance according to claims 1, 3, 4, 5 or 7 to the locus.

* * * * *